(12) United States Patent
Koenig et al.

(10) Patent No.: US 8,105,720 B2
(45) Date of Patent: Jan. 31, 2012

(54) HUMIDITY SENSING DEVICE FOR USE IN FUEL CELL SYSTEMS

(75) Inventors: Christian Koenig, Dreieich (DE); Ulrich Dumke, Ruesselsheim (DE); Rocco Schoene, Nierstein (DE)

(73) Assignee: GM Global Technologies LLC, Detroit, MI (US)

( * ) Notice: Subject to any disclaimer, the term of this patent is extended or adjusted under 35 U.S.C. 154(b) by 1099 days.

(21) Appl. No.: 11/945,530

(22) Filed: Nov. 27, 2007

(65) Prior Publication Data

US 2009/0136788 A1  May 28, 2009

(51) Int. Cl.
*H01M 8/06* (2006.01)
*G01N 5/02* (2006.01)

(52) U.S. Cl. ...................................... 429/413; 73/29.05

(58) Field of Classification Search .................. 429/408, 429/413; 73/29.01, 29.05
See application file for complete search history.

(56) References Cited

U.S. PATENT DOCUMENTS

| | | |
|---|---|---|
| 6,376,111 B1 | 4/2002 | Mathias et al. |
| 6,706,430 B2 * | 3/2004 | Wheat et al. ................... 429/413 |
| 2007/0186619 A1 * | 8/2007 | Butt et al. ..................... 73/29.01 |

* cited by examiner

*Primary Examiner* — Patrick Ryan
*Assistant Examiner* — Muhammad Siddiquee
(74) *Attorney, Agent, or Firm* — Fraser Clemens Martin & Miller LLC; J. Douglas Miller

(57) ABSTRACT

A humidity sensing device for measuring a humidity of a reactant stream in a fuel cell system is provided. The humidity sensing device includes a humidity sensor coupled to a sensor housing. The sensor housing is adapted to selectively move the humidity sensor to an operating position and to a non-operating position in the fuel cell system. A fuel cell system and a method employing the humidity sensing device in the fuel cell system is also provided.

16 Claims, 6 Drawing Sheets

HUMIDITY SENSING DEVICE FOR USE IN FUEL CELL SYSTEMS

FIELD OF THE INVENTION

The present invention relates generally to a fuel cell system and, more particularly, to a humidity sensing device for use in the fuel cell system.

BACKGROUND OF THE INVENTION

A fuel cell has been proposed as a clean, efficient and environmentally responsible power source for electric vehicles and various other applications. In particular, the fuel cell has been identified as a potential alternative for the traditional internal-combustion engine used in modern vehicles.

One type of fuel cell is known as a proton exchange membrane (PEM) fuel cell. The PEM fuel cell typically includes three basic components: a cathode, an anode and an electrolyte membrane. The cathode and anode typically include a finely divided catalyst, such as platinum, supported on carbon particles and mixed with an ionomer. The electrolyte membrane is sandwiched between the cathode and the anode layers to form a membrane-electrode-assembly (MEA). The MEA is often disposed between porous diffusion media (DM) which facilitate a delivery of gaseous reactants, typically hydrogen from a hydrogen source and oxygen from an air stream, for an electrochemical fuel cell reaction. In automotive applications, individual fuel cells are often stacked together in series to form a fuel cell stack having a voltage sufficient to power an electric vehicle.

To maximize an operating efficiency and an amount of electricity produced, it is desirable for the fuel cell to be properly humidified. Over-humidifying the fuel cell can result in an excessive formation of liquid water that impedes the migration of the gaseous reactants to the electrodes, and minimizes the production of electricity. Under-humidifying the fuel cell can dry out the MEA and may limit the proton transport required in the electrochemical fuel cell reaction.

At least one of the hydrogen and the air stream is typically humidified by one of several methods known in the art. For example, in U.S. Pat. No. 6,376,111, hereby incorporated herein by reference in its entirety, a controller utilizes feedback to control the humidity of a fuel cell assembly. A resistance of the fuel cell assembly measured across a converter is used to control the humidity of the fuel cell assembly.

Relative humidity sensors are generally used to measure and control the humidity level in the fuel cell system. Commercially available humidity sensors, such as capacitive sensors with hydrophilic dielectric materials used to convert water vapor concentration into an electric signal, have been used to obtain the relative humidity readings from fuel cell reactant supply conduits. Upon a shut-down of the fuel cell stack, however, a temperature within the conduits is lowered and may reach a dew point. Upon reaching the dew point, liquid water condenses within the conduit and on the humidity sensors. The liquid water on the humidity sensors leads to inaccurate humidity readings or short-term "blinding" upon start-up of the fuel cell system. The exposure to liquid water may also reduce the useful life of the humidity sensors, for example, due to corrosion or a swelling of the hydrophilic components.

To address the known problems of humidity sensors in fuel cell applications, humidity sensors having an optimized corrosion resistance have been employed. Additionally, heating elements have been used in the oxidant conduits to heat an area around the humidity sensors, thereby militating against a formation of liquid water. These solutions have not been desirably effective, however, in optimizing a durability and an accuracy of humidity sensors in fuel cell systems.

There is a continuing need for a humidity sensing device for a fuel cell system that optimizes a durability and an accuracy of the humidity sensor. Desirably, the humidity sensing device militates against a short-term blinding and a long-term corrosion and swelling of the humidity sensor.

SUMMARY OF THE INVENTION

In concordance with the instant disclosure, a humidity sensing device for use in a fuel cell system that optimizes a durability and an accuracy of the humidity sensor, militates against a short-term blinding, and militates against a long-term corrosion and swelling of the humidity sensor, is surprisingly discovered.

In one embodiment, a humidity sensing device for measuring a humidity of a reactant stream in a fuel cell system is provided. The humidity sensing device includes a humidity sensor coupled to a sensor housing. The sensor housing is adapted to selectively expose the humidity sensor to the reactant stream of the fuel cell system.

In another embodiment, the humidity sensing device is disposed in a fuel cell system. The fuel cell system includes a fuel cell stack having a plurality of fuel cells and a reactant inlet. A reactant source is in fluid communication with the reactant inlet and adapted to provide a reactant stream to the fuel cell stack. A water vapor transfer device is in fluid communication with the reactant source and the reactant inlet, and adapted to humidify the reactant stream. The humidity sensing device is in fluid communication with the reactant stream.

In a further embodiment, a method for operating the humidity sensing device in the fuel cell system is provided. The method includes the steps of providing the humidity sensing device and moving the humidity sensor into the operating position prior to a startup of the fuel cell system. The fuel cell system is then started. A humidity of the reactant stream is measured while the humidity sensor is in the operating position. The humidity of the reactant stream is adjusted as desired. Following a period of operation, the fuel cell system is then shut down. The humidity sensor is moved to the non-operating position during the shutdown of the fuel cell system. A short-term blinding and a long-term corrosion of the humidity sensor are thereby militated against.

DRAWINGS

The above, as well as other advantages of the present disclosure, will become readily apparent to those skilled in the art from the following detailed description, particularly when considered in the light of the drawings described hereafter.

DETAILED DESCRIPTION OF THE INVENTION

Figure 1:
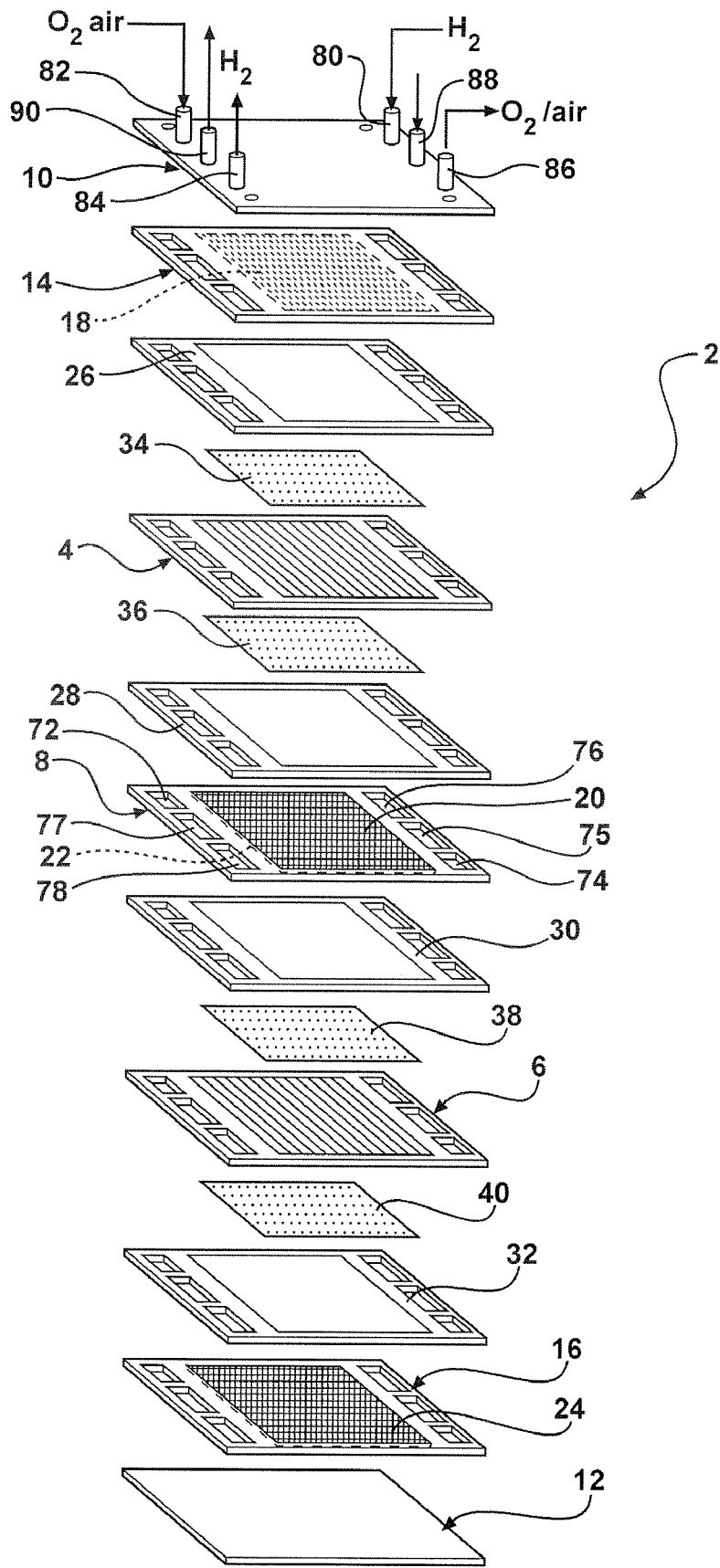
FIG. 1 illustrates a schematic, exploded perspective view of a PEM fuel cell stack of the prior art, showing only two cells.

The following description is merely exemplary in nature and is not intended to limit the present disclosure, application, or uses. It should also be understood that throughout the drawings, corresponding reference numerals indicate like or corresponding parts and features. In respect of the methods disclosed, the steps presented are exemplary in nature, and thus, are not necessary or critical.

FIG. 1 depicts a fuel cell stack 2 having a pair of MEAs 4, 6 separated by an electrically conductive bipolar plate 8. For simplicity, only a two-cell stack (i.e. one bipolar plate) is illustrated and described in FIG. 1, it being understood that the typical fuel cell stack 2 will have many more such cells and bipolar plates.

The MEAs 4, 6 and bipolar plate 8 are stacked together between a pair of clamping plates 10, 12 and a pair of unipolar end plates 14, 16. The clamping plates 10, 12 are electrically insulated from the end plates 14, 16 by a gasket or a dielectric coating (not shown). The unipolar end plates 14, 16, as well as both working faces of the bipolar plate 8, include an active area 18, 20, 22, 24 such as a flow field for distributing gaseous reactant streams over an anode and a cathode, respectively, of the MEAs 4, 6. The gaseous reactant streams typically include hydrogen gas and air or oxygen.

Nonconductive gaskets 26, 28, 30, 32 provide seals and an electrical insulation between the several components of the fuel cell stack 2. Gas-permeable diffusion media 34, 36, 38, 40 abut the anodes and the cathodes of the MEAs 4, 6. The end plates 14, 16 are disposed adjacent the diffusion media 34, 40, respectively, while the bipolar plate 8 is disposed adjacent the diffusion media 36 on the anode face of MEA 4. The bipolar plate 8 is further disposed adjacent the diffusion media 38 on the cathode face of MEA 6.

The bipolar plate 8, unipolar end plates 14, 16, and the gaskets 26, 28, 30, 32 each include a cathode supply aperture 72 and a cathode exhaust aperture 74, a coolant supply aperture 75 and a coolant exhaust aperture 77, and an anode supply aperture 76, and an anode exhaust aperture 78. Supply manifolds and exhaust manifolds of the fuel cell stack 2 are formed by an alignment of the respective apertures 72, 74, 75, 77, 76, 78 in the bipolar plate 8, unipolar end plates 14, 16, and the gaskets 26, 28, 30, 32.

The reactant streams are supplied to the fuel cell stack 2 through inlet conduits in communication with the supply manifolds. For example, the hydrogen gas is supplied to the anode supply manifold via an anode inlet conduit 80. The air is supplied to the cathode supply manifold of the fuel cell stack 2 from a cathode inlet conduit 82. An anode outlet conduit 84 and a cathode outlet conduit 86 are also provided for the anode exhaust manifold and the cathode exhaust manifold, respectively. A coolant inlet conduit 88 is provided for supplying liquid coolant to a coolant supply manifold. A coolant outlet conduit 90 is provided for removing coolant from a coolant exhaust manifold. It should be understood that the configurations of the various inlets 80, 82, 88 and outlets 84, 86, 90 in FIG. 1 are for the purpose of illustration, and other configurations may be chosen as desired.

Figure 2:
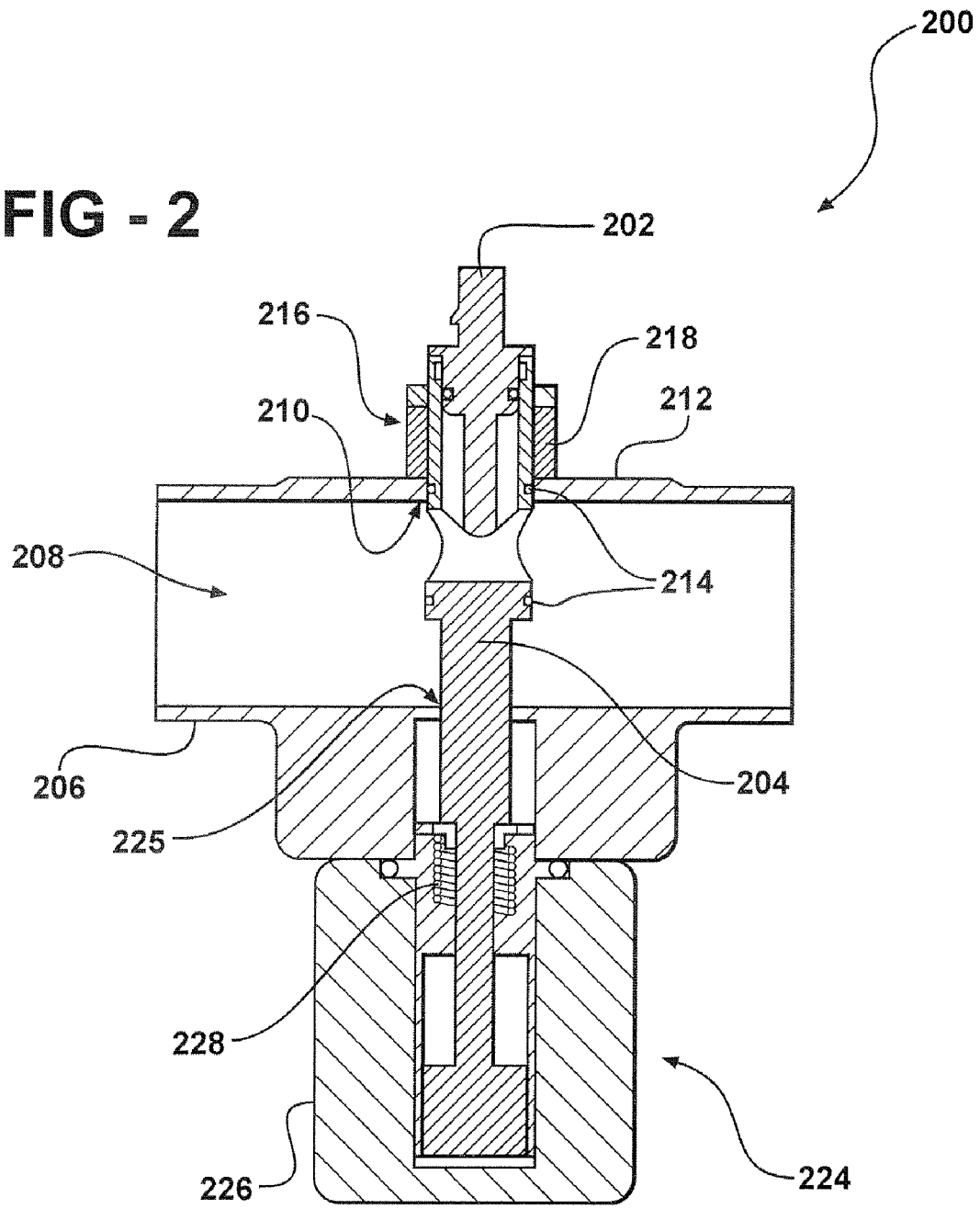
FIG. 2 is a side sectional view of a humidity sensing device in an operating position, according to an embodiment of the disclosure.
Figure 3:
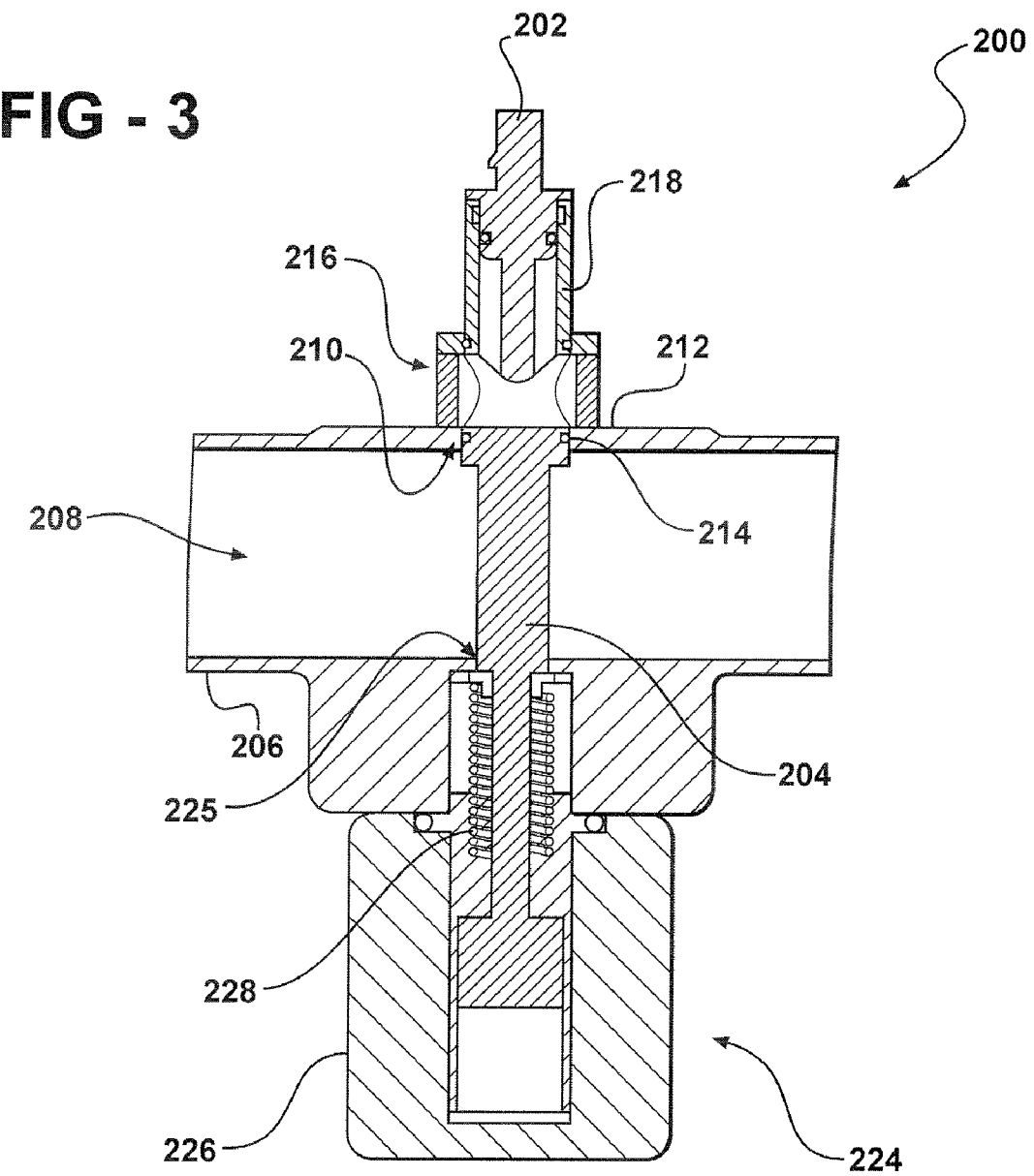
FIG. 3 is a side sectional view of the humidity sensing device shown in FIG. 2, the humidity sensing device in a non-operating position.

FIGS. 2 and 3 show a humidity sensing device 200 adapted for use with the fuel cell stack 2. The humidity sensing device 200 measures a humidity of the reactant stream, such as an air stream or a hydrogen stream, flowing to the fuel cell stack 2. The measured humidity may be a relative humidity, for example. The humidity sensing device 200 includes a humidity sensor 202 coupled to a sensor housing 204.

Figure 4:
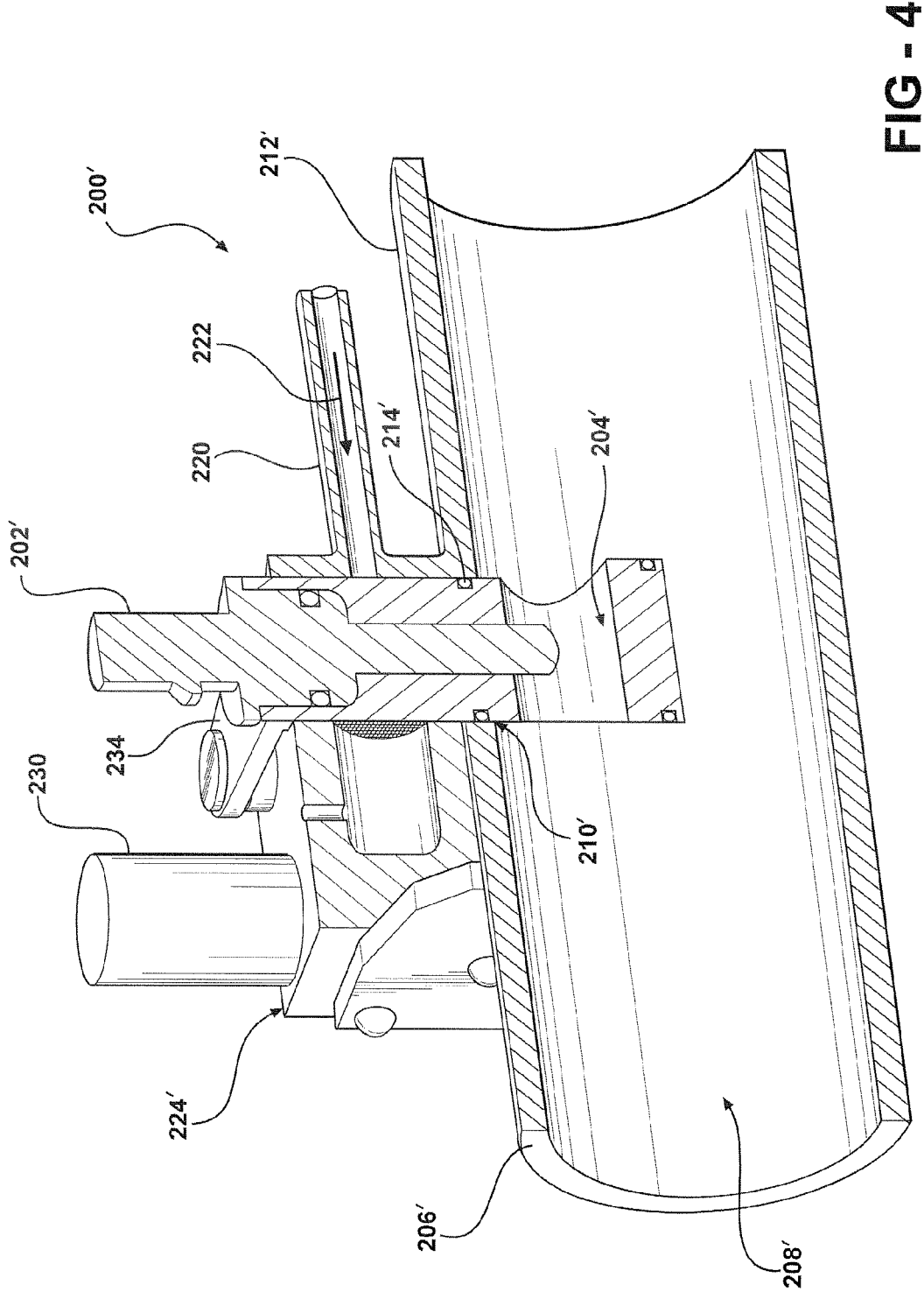
FIG. 4 is a perspective view of a humidity sensing device, partially in section, according to another embodiment of the invention, the humidity sensor in an operating position.
Figure 5:
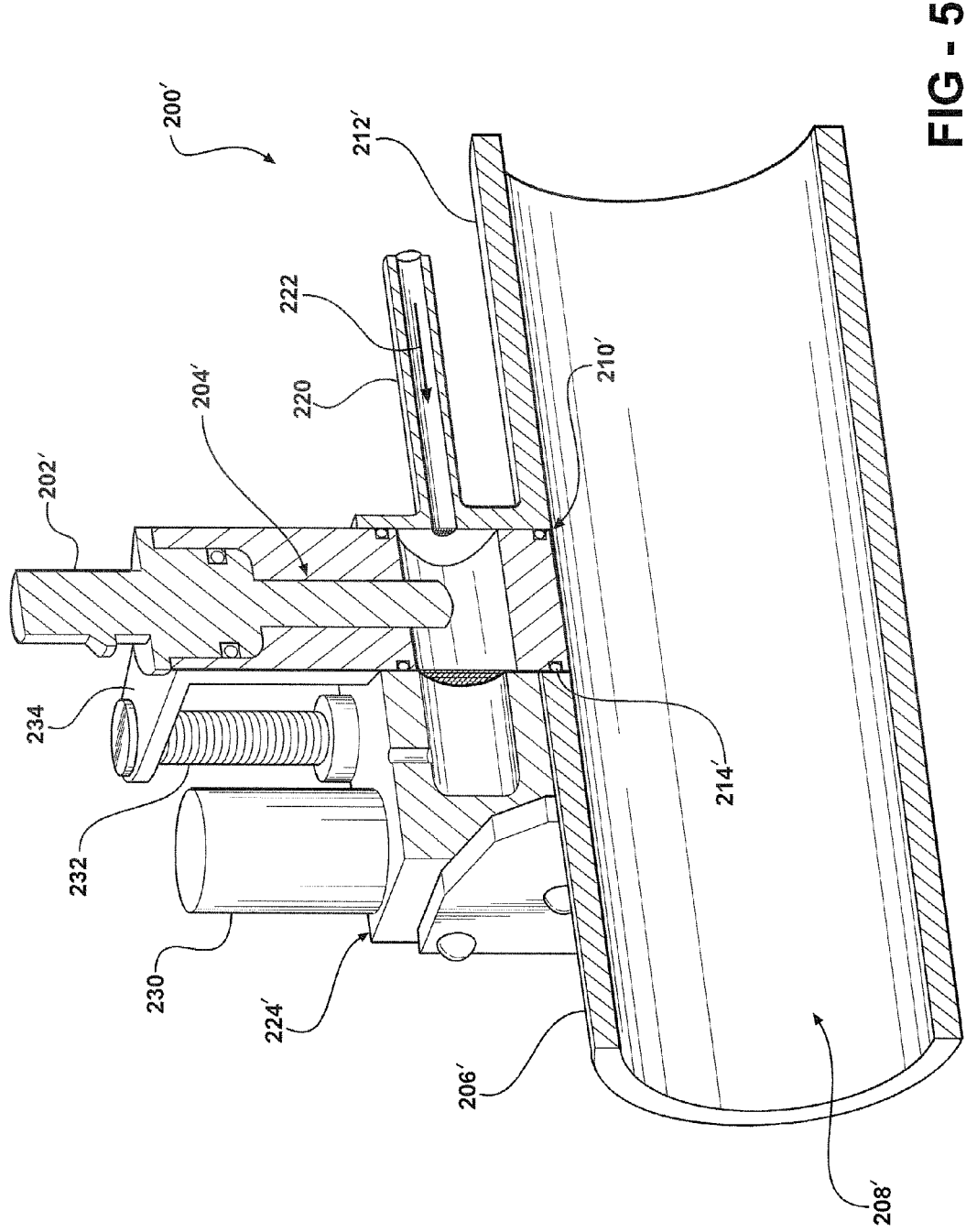
FIG. 5 is a perspective view, partially in section, of the humidity sensing device illustrated in FIG. 4, the humidity sensor in a non-operating position.

The sensor housing 204 is adapted to selectively move the humidity sensor 202 to an operating position, as shown in FIGS. 2 and 4, and to the non-operating position, as shown in FIGS. 3 and 5. In the operating position, the humidity sensor 202 measures the humidity of the reactant stream. In the non-operating position, the humidity sensor 202 is removed from the humidity of the reactant stream.

The humidity sensing device 200 is in fluid communication with the reactant stream being supplied to the fuel cell stack 2. In a particular embodiment, the humidity sensing device 200 is in fluid communication with an air stream being supplied to the cathode supply manifold of the fuel cell stack 2 via the cathode inlet conduit 82. As a nonlimiting example, the humidity sensor 202 is in contact with the reactant stream while in the operating position. As a further nonlimiting example, the humidity sensor 202 is out of contact with the reactant stream while in the non-operating position.

The humidity sensing device 200 further includes a main housing 206. The main housing 206 has a passage 208 extending therethrough. The passage 208 is adapted to transport the reactant stream flowing to the fuel cell stack 2. For example, the passage 208 of the main housing 206 may be in fluid communication with one of the anode inlet conduit 80 and the cathode inlet conduit 82. In an illustrative embodiment, the main housing 206 is in fluid communication with the cathode inlet conduit 82. The main housing 206 may further be formed integrally with one of the anode inlet conduit 80 and the cathode inlet conduit 82. For example, the main housing 206 may be formed from one of the anode inlet conduit 80 and the cathode inlet conduit 82.

The main housing 206 includes a first aperture 210 formed through a wall 212 thereof. The first aperture 210 is in fluid communication with the passage 208. The slide member 204 is slidably disposed in the first aperture 210. The sensor housing 204 is also adapted to selectively move the humidity sensor 202 into the passage 208 through the first aperture 210 when moving the humidity sensor 202 into the operating position.

The sensor housing 204 further includes at least one seal member 214, such as an O-ring and the like. The seal member 214 is configured to provide a substantially fluid tight seal at the first aperture 210 when the humidity sensor 202 is in the operating position and the non-operating position. For example, when the humidity sensor 202 is in contact with the reactant stream, the reactant stream flows through the passage 208 without any substantial leakage of the reactant stream through the first aperture 210. The seal member 214 engages the wall 212 of the main housing 206 adjacent the first aperture 210. When the humidity sensor 202 is out of contact with the reactant stream, the first aperture 210 is likewise sealed against leakage of the reactant stream by an engagement of the seal member 214 with the wall 212.

The humidity sensing device 200 of the present disclosure further includes a drying chamber 216. The drying chamber 216 is disposed adjacent the first aperture 210 in the main housing 206. The drying chamber 216 is adapted to receive the humidity sensor 202 in the non-operating position. While in the non-operating position, the drying chamber 216 dries condensation on the humidity sensor, for example, by exposing the humidity sensor 202 to the ambient atmosphere. In particular embodiments, the drying chamber 216 has at least one filter 218 that filters a drying fluid to militate against a contamination of the humidity sensor 202 while drying in the non-operating position.

Figure 6:
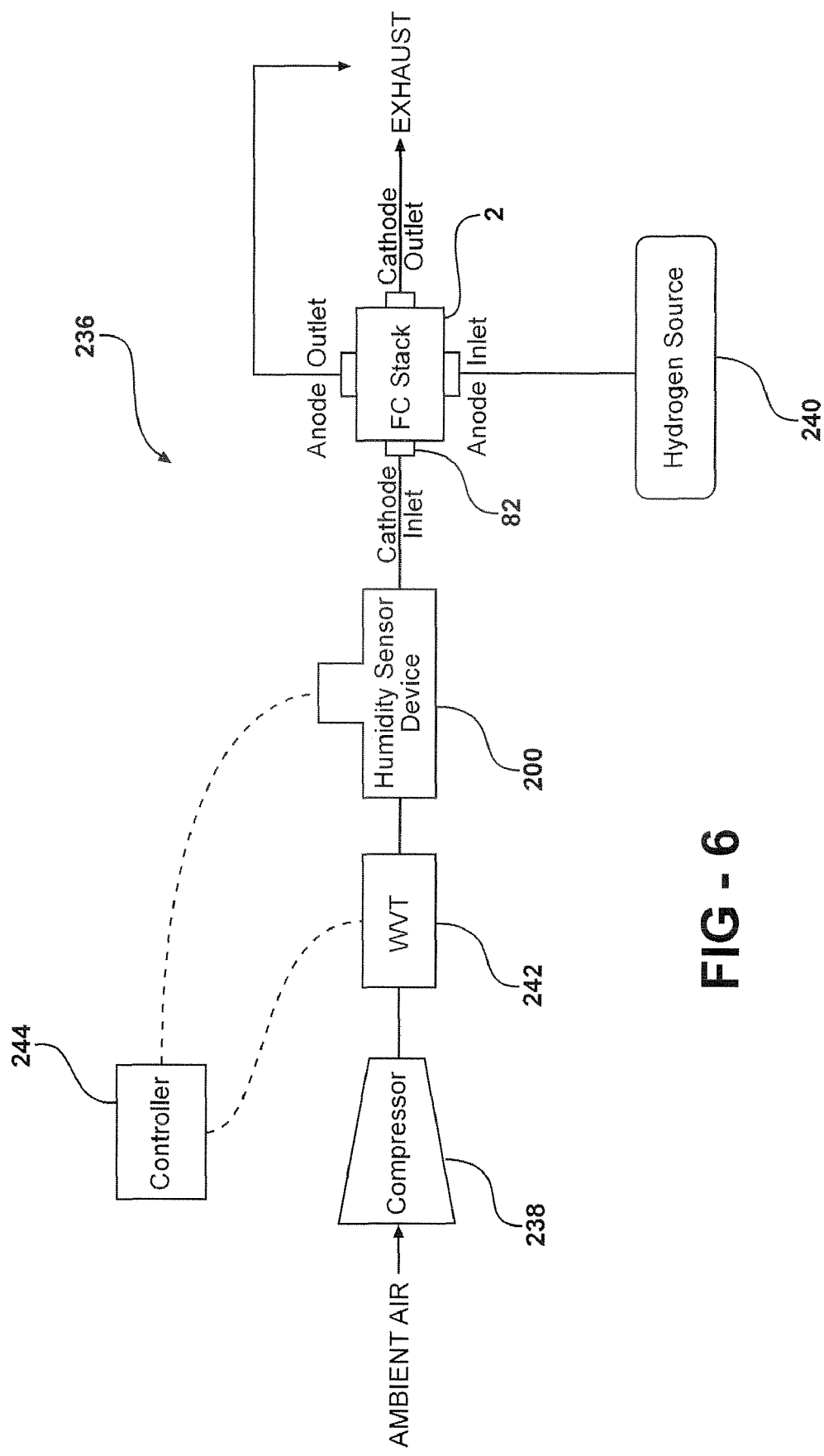
FIG. 6 is a schematic diagram of a fuel cell system having the humidity sensing device according to the present disclosure.

As shown in FIGS. 4 and 5, the drying chamber 216 may be in fluid communication with an air conduit 220 connected to an air compressor (shown in FIG. 6). The air compressor provides a substantially dry air stream 222 as the drying fluid to the humidity sensor 202 in the non-operating position. The humidity sensor 202 may thereby be dried when it is not being used to measure the humidity of the reactant stream in the passage 208.

With renewed reference to FIGS. 2 and 3, the humidity sensing device 200 includes an actuator 224 adapted to selectively move the sensor housing 204. When the actuator 224 is disposed on an opposite side of the main housing 206 as the humidity sensor 202, as shown in FIGS. 2 and 3, the sensor housing 204 may further be disposed through a second aperture 225 formed through the wall 212 of the main housing 206. The second aperture 225 is sealable in the same manner as described herein with regard to the first aperture 210.

In the embodiment shown, the actuator 224 is a magnetic actuator. For example, the actuator 224 may include a magnetic coil 226 adapted to move the humidity sensor 202 into the operating position with magnetic force when a current is applied to the magnetic coil 226. It is understood that other actuator types may be used as desired. The actuator 224 also includes a retainer spring 228. The retainer spring 228 is coupled to the sensor housing 204 and adapted to move the humidity sensor 202 into the non-operating position when the current is not applied to the magnetic coil 226. The retainer spring 228 is adapted to compress and urge the humidity sensor 202 when the magnetic coil 226 is activated and moves the humidity sensor 202 into the operating position. The retainer spring 228 expands and urges the humidity sensor 202 when the magnetic coil 226 is deactivated. The sensor housing 204 is thereby displaced and the humidity sensor 202 is moved into the non-operating position.

A further embodiment of the present disclosure is shown in FIGS. 4 and 5. Like structures repeated from FIGS. 2 and 3 include the same reference numerals with a prime symbol ('). In the further embodiment, the actuator 224' is a mechanical actuator. It is understood other actuator types may be used as desired. As shown in FIGS. 4 and 5, the actuator 224' is disposed adjacent the humidity sensor 202. The actuator 224' includes a motor 230, such as an electric motor or a stepper motor, for example. The motor 230 is coupled to a threaded actuating member 232. The threaded actuating member 232 is further coupled to the sensor housing 204', for example, via a bracket 234. The threaded actuating member 232 selectively moves the sensor housing 204' through the first aperture 210' upon an operation of the motor 230.

As depicted in FIG. 6, the humidity sensing device 200 is particularly useful in a fuel cell system 236. The fuel cell system 236 is configured to adjust the humidity of the reactant stream flowing to the fuel cell stack 2 based on a measured humidity of the reactant stream. In one embodiment, the fuel cell system 236 includes the fuel cell stack 2 having a reactant inlet, such as the cathode supply conduit 82, for example. A reactant source, such as an air compressor 238, is in fluid communication with the reactant inlet. The reactant source is adapted to provide the reactant stream to the fuel cell stack 2.

A water vapor transfer (WVT) device 242 is in fluid communication with the reactant source and the reactant inlet. The WVT device 242 is configured to selectively humidify the reactant stream. The humidity sensing device 200 is in fluid communication with the reactant inlet and the reactant source, so that the humidity sensor 202 may be in contact with the reactant stream when in the operating position.

The fuel cell system further includes a controller 244. The humidity sensor 202 of the humidity sensing device 200 and the controller 244 are in electrical communication. The controller 244 receives the humidity measurements of reactant stream from the humidity sensor 202 while in the operating position. The controller 244 selectively modifies the humidity of the reactant stream, based upon the humidity measurements.

It should be appreciated that the humidity sensing device 200 may be disposed between one of the WVT device 242 and the reactant inlet, and the reactant source and the WVT device 242, as desired. In the particular embodiment shown, the humidity sensing device 200 is disposed between the WVT device 242 and the fuel cell stack 2. The humidity sensing device 200 thereby provides humidity measurements of the humidified reactant stream, such as the air stream compressed from the ambient atmosphere and humidified via the WVT device 242. Accordingly, the reactant stream flowing to the fuel cell stack 2 is maintained at a desired level of humidification.

The present disclosure also contemplates a method for operating the humidity sensor 202 in the fuel cell system 236. The method first includes the steps of providing the humidity sensing device 200 and moving the humidity sensor 202 into the operating position at a startup of the fuel cell system 236. During operation, the humidity of the reactant stream flowing in the fuel cell system 236 is measured. The measured humidity is used to maintain a desired humidity level in the reactant stream.

Following an operation of the fuel cell stack 2, and a measurement of the reactant stream humidity, the fuel cell system 236 is shut down. The shut down step occurs upon a cessation of flow of the reactant stream in the fuel cell system 236, for example. It should be appreciated that upon shutdown of the fuel cell system 236, the conduits through which the reactant streams flow begin to cool. Upon reaching the dew point temperature, water condenses on surfaces in contact with the reactant streams, including the humidity sensor 202 in the operating position. Therefore, following the shutdown of the fuel cell system the humidity sensor 202 is moved into the non-operating position and isolated from the fuel cell system 236 conduits. Upon startup of the fuel cell system 236, the method may be repeated.

The method of the disclosure further includes the step of drying the humidity sensor 202 during the shutdown period of the fuel cell system, i.e., while the humidity sensor is in the non-operating position. The step of drying the humidity sensor 202 may include the step of exposing the humidity sensor to the ambient atmosphere. For example, the ambient atmosphere may include warm, substantially dry air within an engine compartment. In another embodiment, the step of drying the humidity sensor 202 includes the step of flowing a substantially dry stream of air adjacent the humidity sensor 202.

It is surprisingly found that moving the humidity sensor 202 into the non-operating position, and away from condensation in the cooling reactant, militates against a short-term blinding or swelling of the humidity sensor 202 due to water exposure. A maintained accuracy of the humidity sensor 202 is thereby facilitated. A long-term corrosion of the humidity sensor 202 due to exposure to the liquid water condensate is also militated against by drying the humidity sensor 202. The drying results in an optimized durability of the humidity sensor. The step of drying the humidity sensor 202 while in the non-operating position optimizes the operational life of the humidity sensor 202 employed in measuring the humidity of the reactant streams flowing to the fuel cell stack 2.

While certain representative embodiments and details have been shown for purposes of illustrating the invention, it will be apparent to those skilled in the art that various changes may be made without departing from the scope of the disclosure, which is further described in the following appended claims.

What is claimed is:

1. A humidity sensing device for measuring a humidity of a reactant stream in a fuel cell system, comprising:
   a humidity sensor;
   a sensor housing coupled to the humidity sensor, the sensor housing adapted to selectively expose the humidity sensor to the reactant stream of the fuel cell; and
   a main housing having a passage extending there through, the main housing having a wall with an aperture formed therein, the aperture in communication with the passage and adapted to slidably receive the sensor housing therein.

2. The humidity sensing device according to claim 1, wherein the humidity sensor is exposed to the reactant stream in an operating position.

3. The humidity sensing device according to claim 1, wherein the sensor housing is further adapted to selectively move the humidity sensor into the passage through the aperture.

4. The humidity sensing device according to claim 3, wherein the sensor housing includes a seal member adapted to seal against the wall of the main housing when the humidity sensor is in at least one of an operating position and a non-operating position.

5. The humidity sensing device according to claim 1, further comprising an actuator adapted to move the sensor housing.

6. The humidity sensing device according to claim 5, wherein the actuator is a magnetic actuator.

7. The humidity sensing device according to claim 6, wherein the magnetic actuator includes:
   a magnetic coil adapted to magnetically move the humidity sensor into contact with the reactant stream when a current is applied to the magnetic coil; and
   a retainer spring coupled to the sensor housing and adapted to move the humidity sensor out of contact with the reactant stream when the current is not applied to the magnetic coil.

8. The humidity sensing device according to claim 5, wherein the actuator includes a motor coupled to a threaded actuating member adapted to selectively move the sensor housing upon operation of the motor.

9. The humidity sensing device according to claim 4, further comprising a drying chamber for drying the humidity sensor in the non-operating position.

10. The humidity sensing device according to claim 9, wherein the drying chamber is in communication with the ambient atmosphere.

11. The humidity sensing device according to claim 9, wherein the drying chamber includes at least one filter that militates against a contamination of the humidity sensor.

12. The humidity sensing device according to claim 9, wherein the drying chamber is in communication with an air compressor that provides a substantially dry air stream to the humidity sensor in the non-operating position.

13. A fuel cell system, comprising:
   a fuel cell stack including a plurality of fuel cells and a reactant inlet;
   a reactant source in fluid communication with the reactant inlet and adapted to provide a reactant stream to the fuel cell stack;
   a water vapor transfer device in fluid communication with the reactant source and the reactant inlet, the water vapor transfer device adapted to humidify the reactant stream; and
   a humidity sensing device in fluid communication and formed integrally with the reactant stream, the humidity sensing device including a humidity sensor coupled to a sensor housing adapted to selectively move the humidity sensor between an operating position in contact with the reactant stream and a non-operating position out of contact with the reactant stream.

14. The fuel cell system of claim 13, further comprising a controller adapted to receive a signal from the humidity sensor and adjust the humidification of the reactant stream based upon the signal from the humidity sensor.

15. The fuel cell system of claim 13, wherein the reactant source is an air compressor and the reactant stream is an air stream.

16. The fuel cell system of claim 13, wherein the reactant stream is one of an anode conduit and a cathode conduit.

* * * * *